United States Patent [19]

Blanton et al.

[11] Patent Number: 5,557,924
[45] Date of Patent: Sep. 24, 1996

[54] CONTROLLED DELIVERY OF FILTERED CRYOGENIC LIQUID

[75] Inventors: Russell Blanton, Acton; David Tucker, Quincy; Thornton Stearns, Winchester, all of Mass.

[73] Assignee: Vacuum Barrier Corporation, Woburn, Mass.

[21] Appl. No.: 309,531

[22] Filed: Sep. 20, 1994

[51] Int. Cl.[6] .................................................. F17C 7/02
[52] U.S. Cl. ............................ 62/50.1; 62/908; 62/78
[58] Field of Search ................................ 62/18, 38, 50.1, 62/78

[56] References Cited

U.S. PATENT DOCUMENTS

| | | | |
|---|---|---|---|
| 2,737,784 | 3/1956 | Becker et al. | 62/38 |
| 3,192,730 | 7/1965 | Webb | 62/15 |
| 3,237,418 | 3/1966 | Meisler | 62/14 |
| 3,442,091 | 5/1969 | Klipping et al. | 62/50.1 X |
| 3,595,788 | 7/1971 | Knippenberg et al. | 62/42 X |
| 3,683,589 | 8/1972 | Seitz et al. | 62/18 X |
| 3,815,376 | 6/1974 | Lofredo et al. | 62/22 |
| 4,051,886 | 10/1977 | Ross | 164/16 |
| 4,065,278 | 12/1977 | Newton et al. | 62/26 |
| 4,152,130 | 5/1979 | Theobald | 62/18 |
| 4,237,699 | 12/1980 | Longsworth et al. | 62/51.2 |
| 4,620,962 | 11/1986 | Brodbeck | 62/78 X |
| 4,715,187 | 12/1987 | Stearns | 62/51.1 X |
| 4,717,406 | 1/1988 | Giacobbe | 62/18 |
| 4,759,848 | 7/1988 | Segura et al. | 210/651 |
| 4,878,354 | 11/1989 | Stearns | 62/63 |
| 5,122,175 | 6/1992 | Koyama et al. | 62/38 |
| 5,228,269 | 7/1993 | Sanfilippo et al. | 53/432 |
| 5,271,232 | 12/1993 | Ogawa | 62/50.1 |
| 5,272,881 | 12/1993 | Lee | 62/50.4 |

FOREIGN PATENT DOCUMENTS

| | | |
|---|---|---|
| 3533016A1 | 3/1987 | Germany . |
| 1070395A | 1/1984 | U.S.S.R. . |
| 2169998 | 7/1986 | United Kingdom . |

OTHER PUBLICATIONS

Abrikosova et al., "Purity of Liquid Helium", 1970 Consultants Bureau.
Belov et al., Chem. Abstracts, vol. 94, No. 14, Apr. 6, 1981.
Cheung et al., "Efficiently Produced Ultra–high–purity Nitrogen On–site", Chemical Engineering Progress, Oct. 1991.
Lee, "Liquid Nitrogen and Wafer Fabrication Problems", pp. 94–97, Solid State Technology, Dec. 1981.

*Primary Examiner*—Christopher Kilner
*Attorney, Agent, or Firm*—Fish & Richardson, P.C.

[57] ABSTRACT

A system for delivering a controlled stream of purified liquid cryogen from an outlet. The system includes a cryogen delivery flow path that is made up of a delivery conduit connecting a source of liquid cryogen to the outlet. A cryogen purifier positioned in a section of the conduit, is capable of purifying (sterilizing) liquid cryogen flowing therethrough, and a section of the delivery conduit downstream of the cryogen purifier is clean (sterile). The system also includes a cleansing flow path for cleansing (sterilizing) the cryogen purifier and the clean delivery conduit section. The cleansing flow path includes a cleansing conduit connecting a source of cleansing (sterilizing) medium to the delivery conduit and the cryogen purifier. The cryogen purifier and clean delivery conduit section are isolated from the cryogen source during conduit cleansing, and cleansing is accomplished without subjecting the cryogen source to the cleansing medium.

24 Claims, 6 Drawing Sheets

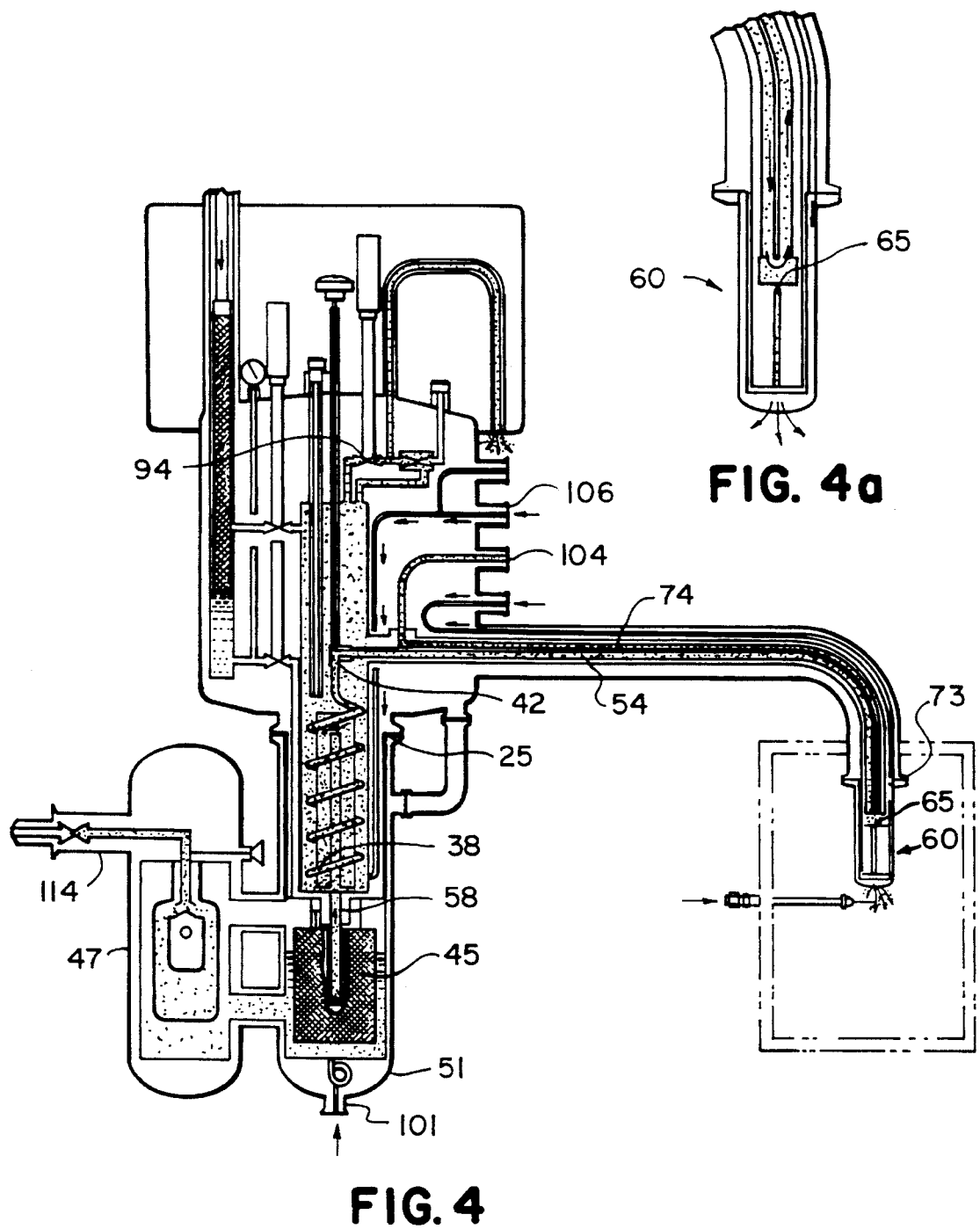

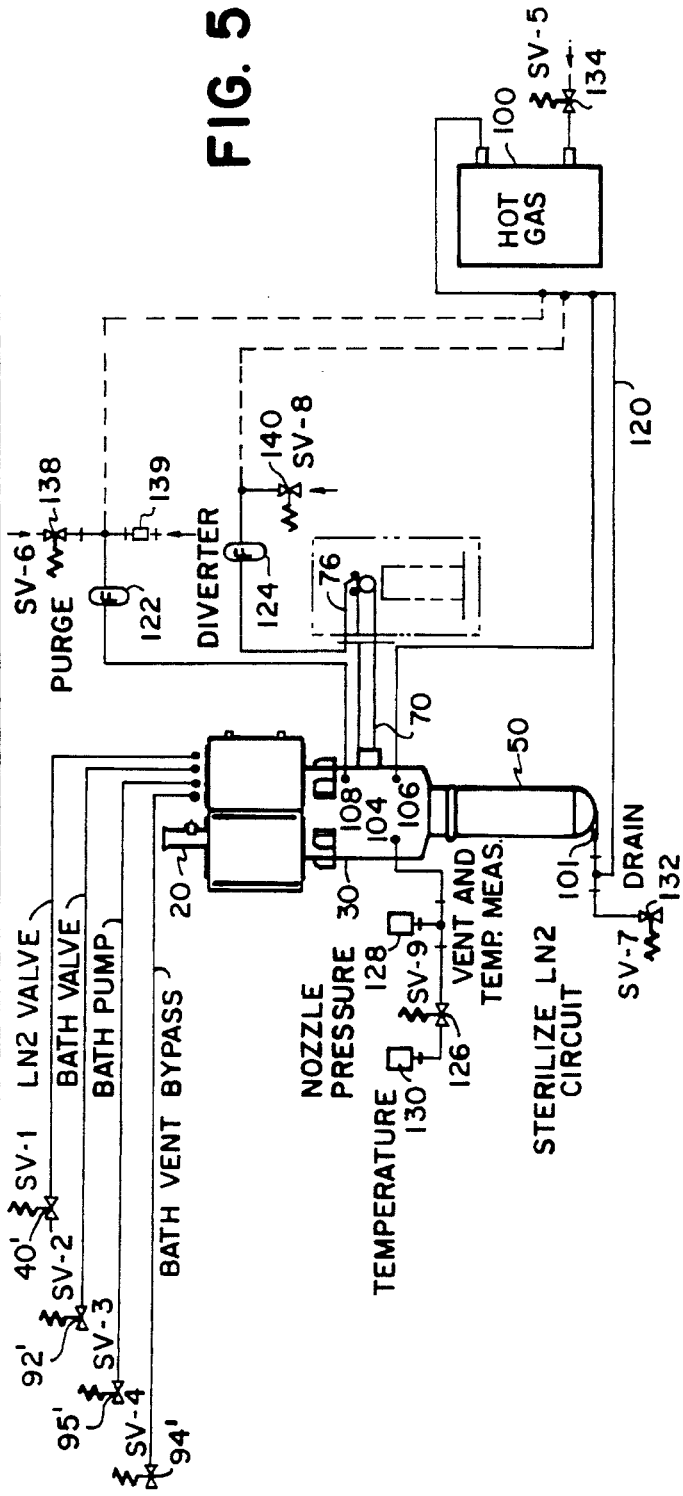

FIG. 5

| VACUUM BARRIER CORPORATION | ASEPTIC INJECTOR INTERCONNECTIONS | | | | | | | | | | | |
|---|---|---|---|---|---|---|---|---|---|---|---|---|
| CONDITION | 40 | 92 | 95 | 94 | 134 | 138 | 132 | 140 | 126 | 120 | 42 | 139 | 114 |
| START-UP COOLDOWN | CLOSED | OPEN | OFF | OPEN | CLOSED | OPEN | CLOSED | OPEN | CLOSED | CLOSED | CLOSED | CLOSED | OPEN |
| NORMAL OPERATION LN2 STREAM ON | OPEN | CYCLING | ON | CLOSED | CLOSED | OPEN | CLOSED | CYCLING | CLOSED | CLOSED | OPEN | OPEN | OPEN |
| NORMAL OPERATION LN2 STREAM OFF | CLOSED | CYCLING | ON | CLOSED | CLOSED | OPEN | CLOSED | CYCLING | CLOSED | CLOSED | OPEN | CLOSED | OPEN |
| DRAIN- STERILIZE OFF | CLOSED | CLOSED | OFF | CLOSED | CLOSED | CLOSED | OPEN | CLOSED | OPEN | OPEN | OPEN | CLOSED | OPEN |
| STERILIZE ON | CLOSED | CLOSED | OFF | CLOSED | OPEN | CLOSED | OPEN | CLOSED | OPEN | OPEN | OPEN | CLOSED | CLOSED |

CONTROLLED DELIVERY OF FILTERED CRYOGENIC LIQUID

BACKGROUND OF THE INVENTION

This invention relates to apparatus and methods for controlled delivery of purified cryogenic liquid, such as liquid nitrogen.

In various applications, it is important to deliver a metered amount of cryogenic liquid. For example, thin-wall containers, such as plastic, aluminum or steel beverage cans, can be used to contain non-carbonated beverages by adding a metered amount of inert cryogenic liquid immediately before capping the can. When vaporized, the inert cryogen increases internal can pressure which strengthens it, helping the can resist collapse, for example, when stacked for storage or for transport.

Controlled delivery is important in such applications. Too little cryogen will not provide adequate pressure (strength), and the can may fail to withstand forces encountered in stacking and shipping. Too much cryogen can create excessive internal can pressure, deforming the can and possibly exploding it. Commonly owned U.S. Pat. No. 4,715,187 discloses apparatus for controlled delivery of liquid cryogen.

In some applications, the cryogenic liquid must be extremely pure, and it is important to remove impurities found in standard large scale sources of cryogen. Some applications, e.g., where the cryogen is mixed with a food or beverage that can support microbial growth, require sterile liquid cryogen. In that case, the purification involves removing microorganisms. Filtration is one useful way to purify and/or sterilize cryogen.

Medical uses of cryogenic liquids may also require filtering or sterilization. For example, oxygen used by hospitals is often transported and stored as a cryogenic liquid to reduce storage space requirements. The liquid is vaporized when sterile gaseous oxygen is needed.

Other applications requiring filtered cryogenic liquids include uses involving semiconductor chip fabrication. Such processes require extreme cleanliness.

Brodbeck U.S. Pat. No. 4,620,962 discloses apparatus for sterilizing vaporized liquid cryogen. Segura U.S. Pat. No. 4,759,848 discloses sterilization of cryogen by filtration.

Sterile delivery systems are required for the delivery of cryogenic liquids to aseptically packaged products, e.g., products packaged in an aseptic food packaging assembly line. When such delivery systems are shutdown and flow through the sterilized delivery system is interrupted, microbial contaminants may get into the sterilization system.

SUMMARY OF THE INVENTION

We have discovered apparatus and methods for metered delivery of purified liquid cryogen, involving periodic cleansing of portions of the delivery system while isolating the cryogen source from the cleansing process. Isolating the cryogen source reduces the time required to cycle between cryogenic delivery at extremely low temperatures and cleansing at higher temperatures. Our discovery is particularly useful for sterilizing the delivery system, e.g., at elevated temperatures, in which case, the system must be quickly cycled between cryogen delivery temperatures and sterilization temperatures.

In one embodiment we have designed apparatus that particularly facilitates rapid temperature cycling of the purification region of the cryogen delivery path. The cryogen, as a saturated liquid, is purified (filtered) in this region. As the system is designed to purify a saturated cryogenic liquid, the purification region of the cryogen delivery path need not be surrounded by a subcooling apparatus. The absence of surrounding subcooling apparatus enables rapid temperature cycling between cryogenic temperature and cleansing/sterilizing temperature. Filtration of saturated liquid cryogen does not unacceptably slow the flow of cryogen through the device, and adequate liquid flow is maintained, even though heat leaks in the filtration region occur and the cryogen is in liquid/vapor equilibrium in that region. Because the apparatus need not be surrounded in that region by a subcooling apparatus, the apparatus is easier to construct and the purification region is more accessible for maintenance. These findings permit a more efficient system for delivering cryogen from a source through a delivery flow conduit to an outlet.

One aspect of the invention generally includes a cryogen purifier positioned in a section of the delivery flow conduit, capable of purifying fluid flowing therethrough. Downstream of the cryogen purifier, the delivery flow conduit includes a clean delivery conduit section. The system also includes a cleansing flow path to cleanse the cryogen purifier and the clean delivery conduit section. Specifically, the cleansing flow path includes a cleansing conduit communicating between a source of cleansing medium and a connection to the cryogen delivery flow path. An on/off valve is positioned between the connection and the cryogen source, and the valve separates the cryogen purifier from the cryogen source. In that way, the cryogen purifier and the clean delivery conduit section can be isolated from the liquid cryogen source during cleansing such that cleansing occurs without subjecting the liquid cryogen source to the cleansing medium.

In preferred embodiments of the system, the cryogen purifier is a cryogen sterilizer capable of sterilizing fluid flowing therethrough, and the clean delivery conduit section is a sterile delivery conduit section. The cleansing medium is a sterilization medium, with the ability to sterilize the cryogen sterilizer and the sterile delivery conduit section. The cleansing flow path is a sterilizing flow path, and the cleansing conduit is a sterilization conduit.

The cryogen sterilizer is a filter sized to sterilize the fluid passing therethrough, e.g., hydrophobic polytetrafluoroethylene (PTFE) filter having pores sized e.g., at 0.2 micron or less, to remove microbial contaminants. The sterilizing medium can be a sterile inert gas and the sterilization conduit is suitable for conveying the sterile inert gas. For example, the system may include a heater capable of raising the temperature of the sterile inert gas to a temperature that kills microbial contaminants. The system may include a gas valve which regulates delivery of the sterilizing medium to the cryogen sterilizer and the sterile delivery conduit section, and the sterilization conduit may connect to the delivery conduit at the cryogen sterilizer. Since the sterile section of the delivery conduit may include a flow control restriction to meter cryogen flow, a sterilization by-pass conduit may be positioned to connect a point in the sterile delivery conduit section upstream of the flow control restriction with an outlet. The by-pass conduit thus increases flow of the sterilizing medium through the cryogen sterilizer during the sterilization cycle. The by-pass conduit may include means for verifying flow of sterilizing medium through the system, e.g., a temperature sensor positioned adjacent to the sterilization medium outlet to measure the temperature of the sterilizing media. A drain valve regulates drainage of liquid cryogen from the cryogen sterilizer before sterilization.

Fluid flowing through the cryogen sterilizer sustains heat leak so the cryogen fluid is saturated at the sterilizer/filter. Vapor in the saturated fluid may be vented through a float valve. The system also includes a bath containing liquid cryogen which subcools sterile liquid cryogen in the sterile delivery conduit section, and means to supply liquid cryogen to, and to maintain liquid cryogen in, the bath. The gas valve may also regulate entry of hot gas into the bath to heat the bath during sterilization. A vent valve regulates venting of hot gas from the bath during sterilization.

A second aspect of the invention generally features methods for delivering a controlled stream of purified liquid cryogen from an outlet, using the above described system. In the method, liquid cryogen is delivered from the source through the cryogen purifier and the clean delivery conduit section downstream of the purifier to the outlet; and, periodically, the cryogen purifier and the clean delivery conduit section are cleansed by delivering a cleansing medium to a connection to the delivery flow path positioned downstream of the on/off valve while the on/off valve is closed. As noted, the cryogen purifier and the clean delivery conduit section are isolated from the liquid cryogen source during purification, and purification occurs without subjecting the liquid cryogen source to the cleansing medium.

In preferred embodiments of the method, the cryogen purifier is a cryogen sterilizer capable of sterilizing fluid flowing therethrough, and the clean delivery conduit section is a sterile delivery conduit section. The cryogen sterilizer and the sterile delivery conduit section are cleansed by sterilization by the cleansing medium in the form of a sterilization medium flowing therethrough. The cleansing flow path is a sterilizing flow path, and the cleansing conduit is a sterilization conduit.

Liquid cryogen flowing through the delivery flow path is stopped by closing the on/off valve, liquid cryogen in the delivery flow path is drained by opening a drain valve, and a gas valve is opened to introduce the sterilizing medium. The sterilizing medium comprises a source of sterile nitrogen gas which is heated to a temperature sufficient for sterilization and delivered into the cryogen sterilizer and the sterile delivery conduit section. Preferably, the cryogen sterilizer is a filter as described above, and the liquid flowing through the filter is saturated.

Other features and advantages of the invention will be apparent from the following description of the preferred embodiment thereof, and from the claims.

BRIEF DESCRIPTION OF THE DRAWINGS

FIGS. 4 and 4a are schematic diagrams of the delivery system of FIG. 1 during sterilization mode.

FIG. 5 is a representation of the valves of the invention and the status of the valves during different modes of operation of the invention.

DESCRIPTION OF THE PREFERRED EMBODIMENTS

Figure 1:
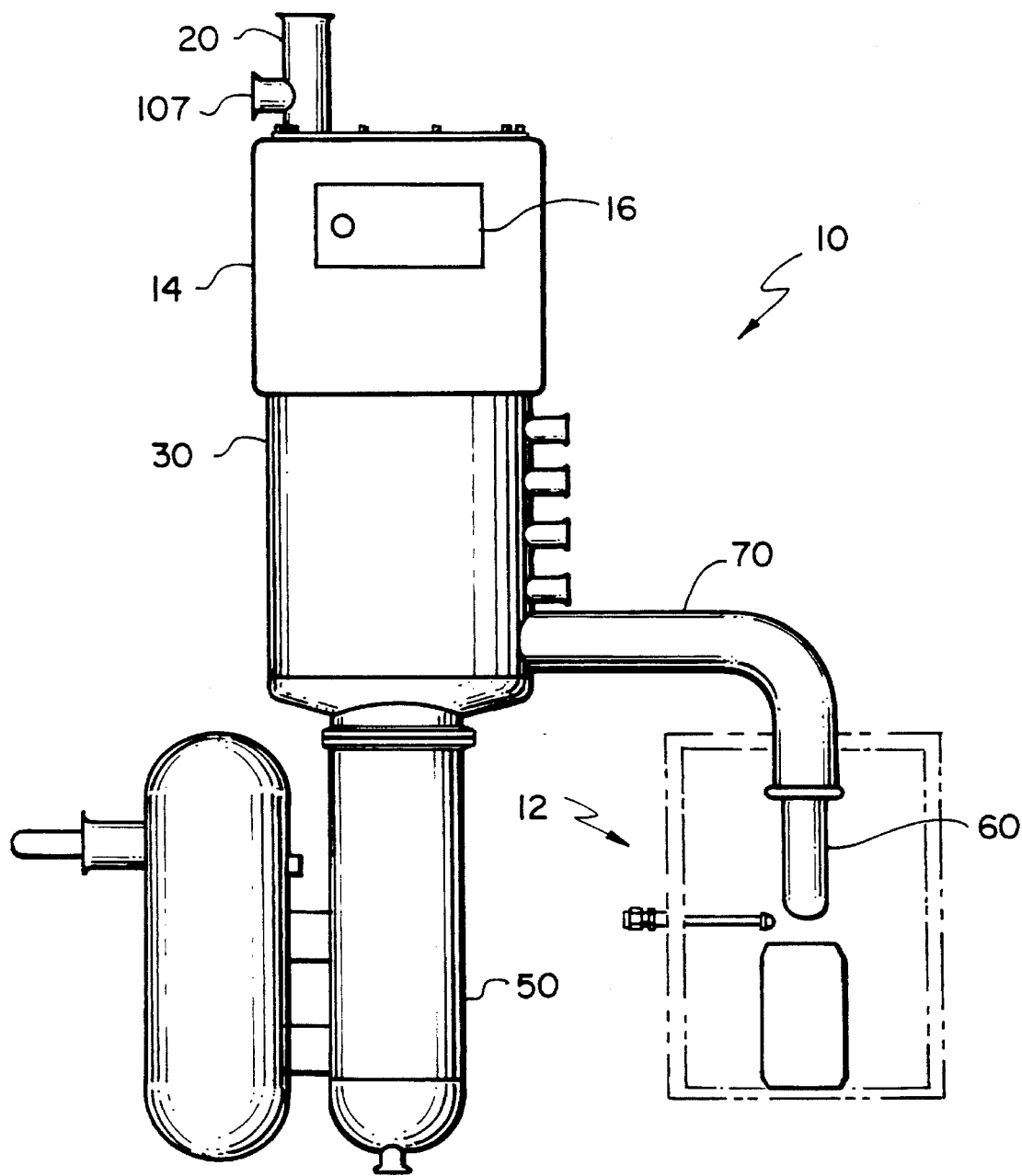
FIG. 1 is a side view of a sterile cryogenic liquid delivery system.

The sterile cryogenic liquid delivery system 10 shown in FIG. 1 controls flow of cryogen from a liquid cryogen source to a nozzle 60. Typically, nozzle 60 delivers liquid cryogen to a filling area 12, e.g., a container filling and capping line, in much the same manner as the nozzle described in commonly owned U.S. Pat. No. 4,715,187, which is hereby incorporated by reference. Specifically, the assembly line may involve sterile packaging for food that supports microbial growth, such as milk. The basic elements of the system include a lower housing 50 positioned in the flow path of a cryogenic fluid between an upper housing 30 and a delivery arm 70.

Nozzle 60 may be oriented vertically as shown in FIG. 1 or generally horizontally, optionally with a vertical pitch, as shown in U.S. Pat. No. 4,715,187 depending on space constraints and ease in matching high speed can filling lines.

For convenience, the system will be described for use with liquid nitrogen, but it will be apparent that other cryogenic liquids could be used as well. Unless otherwise designated, upper housing 30, lower housing 50 and delivery arm 70 are welded stainless steel.

Figure 6:
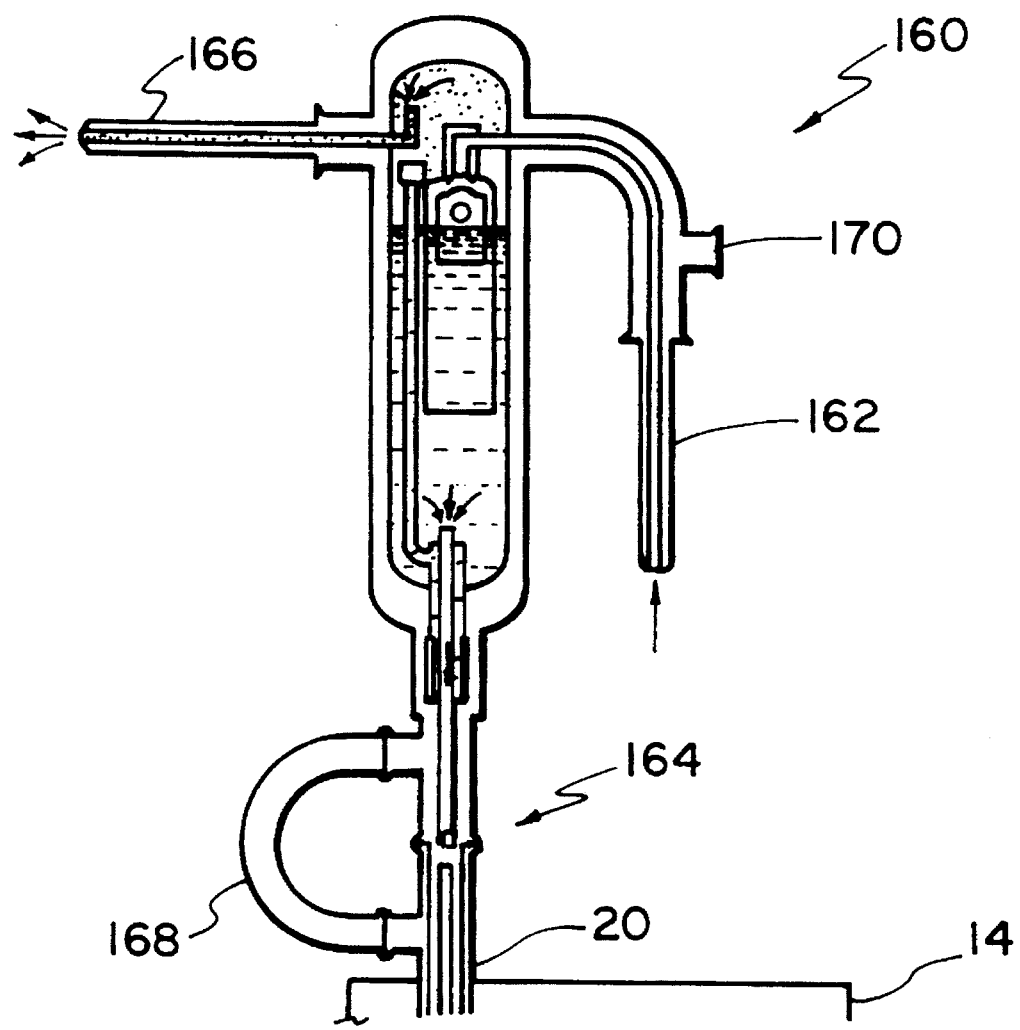
FIG. 6 is a schematic diagram of a local phase separator for use with the delivery system.

Upper housing 30 is similar to the design described in U.S. Pat. No. 4,715,187. A cover 14 includes door 16 which allows access to valve controls located therein. Liquid nitrogen is delivered to a bayonet connector 20 from a constant pressure source (not shown), e.g., from a phase separator through a triax conduit or from an integrated local phase separator 160 (FIG. 6). The triax conduit and bayonet connector 20 are more fully described elsewhere. See, U.S. Pat. No. 3,972,202, hereby incorporated by reference.

Liquid cryogen feed pressure into system 10 is dependent on the elevation of the supply reservoir above the system and follows a relationship of 0.35 PSI per foot of elevation. The natural recirculation of triax piping results in some subcooling of the cryogen as liquid descends from a low pressure region above to a higher pressure at the inlet to bayonet connector 20. This serves to maintain a constant gravity head of pure liquid at the inlet.

Figure 2:
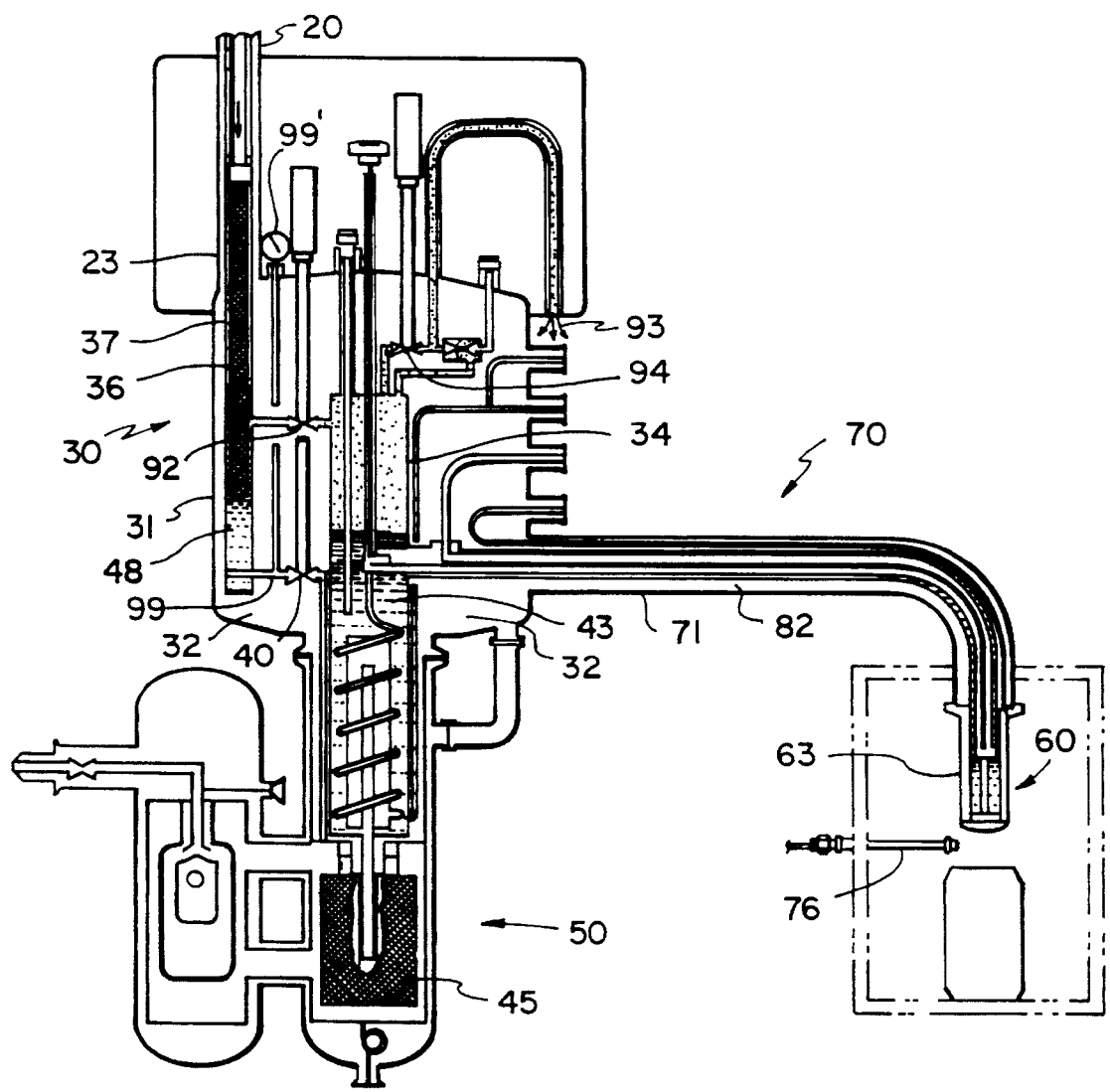
FIG. 2 is a schematic diagram of the delivery system of FIG. 1 during cool-down mode.

Referring to FIG. 2, upper housing 30 has an inner chamber wall 34 surrounded by an outer wall 31 forming vacuum space 32; vacuum space 32 also runs along arm 70 between an outer wall 71 and an inner wall 82. A vacuum pump (not shown) capable of reaching a pressure of $1 \times 10^{-5}$ torr is connected to a vacuum port 107 (FIG. 1) to maintain the vacuum within vacuum space 32.

A tube 37 connects to bayonet connector 20 and resides within upper housing 30. Within tube 37 resides a sintered stainless steel prefilter 36. Prefilter 36 functions as a gross filter prior to the sterile filtration described below. The pore size of prefilter 36 has a nominal rating of, e.g., 0.5 microns.

Liquid nitrogen maintained in a phase separator at a preselected level at the boiling point temperature of liquid nitrogen at atmospheric pressure is delivered into upper housing 30 as described in U.S. Pat. No. 4,715,187. Liquid nitrogen flowing out of bayonet connector 20 passes through prefilter 36, and enters space 48 located within tube 37. From space 48, the cryogen is separated into two pathways. One pathway is the delivery path to nozzle 60, and the other is a subcooling path surrounding the delivery path downstream of a sterilization means 45. The delivery path take-off is on/off valve 40 and the subcooling path take-off is bath valve 92.

Pressure in the subcooling path is maintained at or lower than atmospheric pressure with the result that the pressure experienced by liquid in the subcooling path is slightly lower than the pressure experienced by liquid in the delivery path. Due to the pressure difference, the liquid/vapor equilibrium temperature of the liquid in the subcooling path is slightly below the liquid/vapor equilibrium temperature of liquid in the delivery path. The subcooling path thus subcools the cryogen in the delivery path downstream of sterilization means 45, avoiding vaporization in this section of the delivery path and avoiding flashing at nozzle 60.

There are three modes of operation of system 10: cooldown, operational and sterilization. Before system 10 can deliver sterile cryogen to a filling area, the system itself must be sterilized followed by a cool down period. For ease of description, the cool-down mode is described first.

Referring to FIGS. 2 and 5, during cool-down, liquid nitrogen flows into the subcooling path. Specifically, liquid nitrogen in space 48 flows through bath valve 92 into a bath 43 located within inner wall 34 of upper housing 30 and within inner wall 82 of arm 70. Until the system has reached liquid nitrogen temperature, gas within bath 43 is vented out a vent 93 by opening by-pass valve 94 controlled by by-pass valve control 94' located in a separate control panel (not shown). This keeps cool down periods to a minimum.

The liquid nitrogen level in bath 43 is controlled by a sensor 102 which senses when the liquid nitrogen in bath 43 has reached a desired level signalling the end of cool down mode, and regulates bath valve control 92' located in the control panel (not shown), cycling bath valve 92 between open and closed to maintain the desired liquid nitrogen level in bath 43. Sensor 102 is a capacitance type sensor which determines whether the media between two concentric stainless steel tubes is liquid or vapor, the vapor having a different capacitance from liquid. An important characteristic of this type of level control probe is its ability to withstand the high temperatures of heat sterilization.

Also during cool-down, room temperature gas flows through purge by-pass valve 138 to a purge housing 63, and through diverter valve 140 to a diverter 76 as described below. Valves 92, 94, 138 and 140 are the only open valves during cool-down.

Figures 3, 3A:
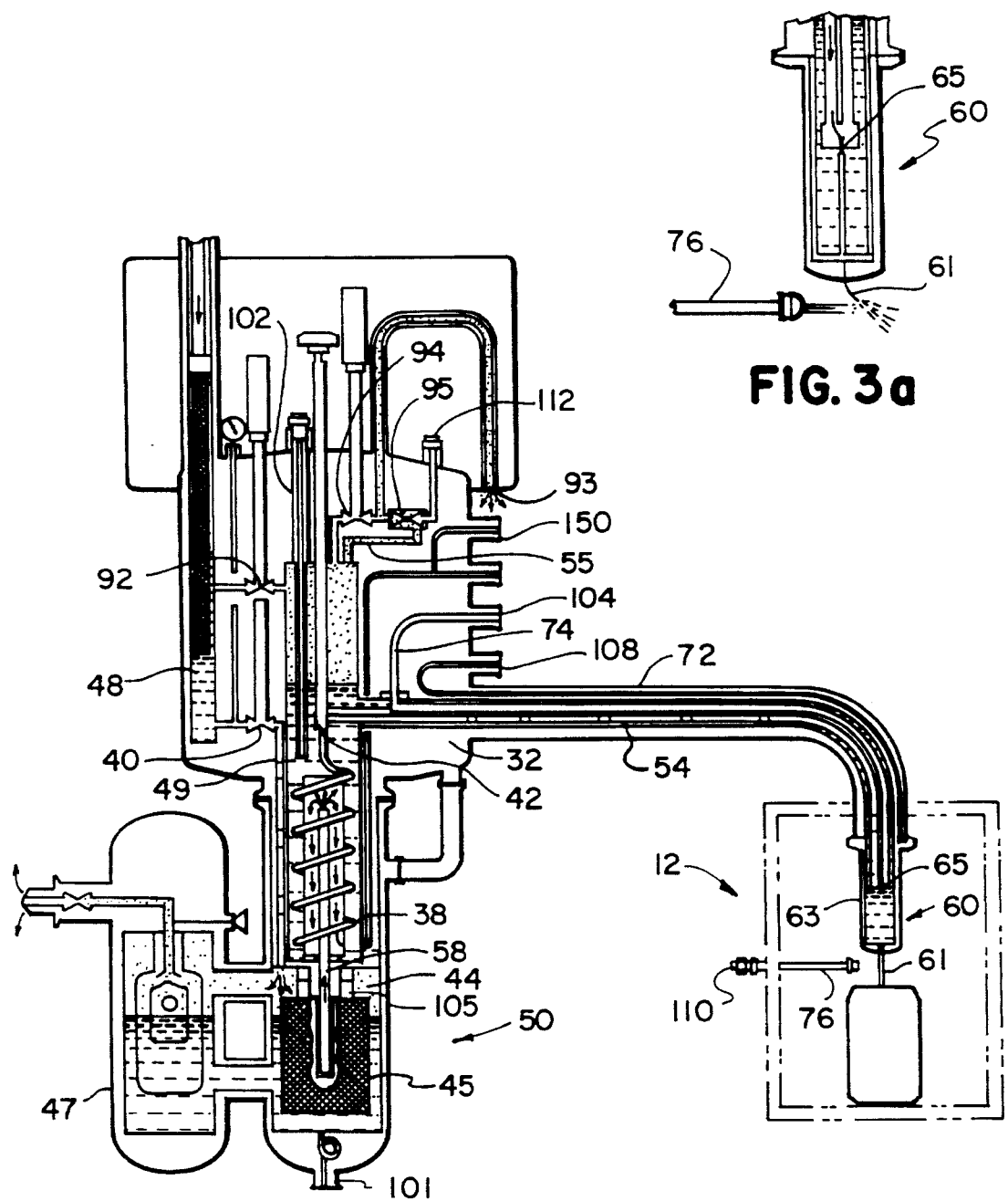
FIGS. 3 and 3a are schematic diagrams of the delivery system of FIG. 1 during operational mode.

Operational mode is entered after the system has reached liquid nitrogen temperature. Flow in the subcooling path continues, maintaining a desired liquid nitrogen level in bath 43. Referring to FIGS. 3 and 5, in operational mode, liquid nitrogen enters the delivery path through on/off valve 40 regulated by on/off valve control 40' (not shown) located in the control panel (not shown). The liquid nitrogen feed pressure at on/off valve 40 is monitored at a pressure tap 99 to verify the feed pressure into the system. This reading, in conjunction with a pressure reading taken downstream of sterilization means 45 (described below), allows monitoring of sterilization means 45 for blockage. The output from tap 99 is measured by a pressure transducer 99'.

Liquid nitrogen in space 48 flows through on/off valve 40 into pipe 49 to a reservoir 44 in lower housing 50. The delivery path to this point is not surrounded by the subcooling path and is in fact sustaining heat leak from both on-off valve 40, a bayonet joint 105 surrounding sterilization means 45 and a drain trap 101 located at the bottom of lower housing 50. The slight subcooling described above resulting from the triax recirculation of the feed plumbing is completely lost and the nitrogen within reservoir 44 is saturated and boiling.

Gaseous nitrogen which evolves in reservoir 44 is allowed to vent out through a float valve 47 which maintains a desired liquid level within reservoir 44. The flow of gas out float valve 47 may be measured, demonstrating that the liquid flowing through sterilization means 45 is in equilibrium with vapor, i.e., the liquid is not sub-cooled.

Returning to the delivery flow path, liquid nitrogen in reservoir 44 enters sterilization means 45, e.g., a 0.2 micron hydrophobic polytetrafluoroethylene filter which removes non-sterile particulates from the liquid nitrogen. Once inside filter 45, liquid nitrogen flows under pressure up through a conduit 58 which extends downward to the lower region of filter 45. Since conduit 58 extends well below the liquid level being maintained in reservoir 44, only pure liquid will flow up conduit 58. Conduit 58 leads sterilized liquid nitrogen to coil 38. From this point, the delivery path is surrounded by the subcooling path. Liquid nitrogen flows through coil 38 where it is cooled to several degrees below saturation temperature and into a metering valve 42 where the downstream pressure can be adjusted to regulate flow out to nozzle 60. Metering valve 42 is externally manually adjusted by control 42'. Subcooled liquid nitrogen flows through metering valve 42 into a conduit 54 and through a flow-control restriction 65 prior to exiting nozzle 60.

Nozzle purge housing 63 maintains a continuous flow of sterile gas, e.g., nitrogen gas at room temperature, 10 cubic feet/hour (CPH) at 40 PSIG, filtered by gas filter 122, around the nozzle to prevent moisture condensation within nozzle 60. The gas is conveyed to the housing through a flow restrictor 139, connected to port 108 on the exterior of upper housing 30, leading to a tube 72 that passes within vacuum space 32 and out to nozzle 60. Diverter 76 is a gas jet device which can deliver a small high velocity flow of sterile nitrogen gas across the path of the liquid nitrogen stream 61 exiting nozzle 60 and instantaneously interrupt its flow (FIG. 3a), as described in U.S. Pat. No. 4,715,187. Gas passes through diverter valve 140 and filter 124 and enters diverter 76 at port 110.

As described above, the temperature of the liquid nitrogen in bath 43 is maintained below the liquid/vapor equilibrium temperature of liquid nitrogen in the delivery conduit by increasing the pressure differential between bath 43 and the delivery path. This increased pressure differential is achieved by reducing the pressure in bath 43 below (ambient) atmospheric pressure. The pressure reduction is achieved by closing by-pass valve 94 and passing gas, e.g. 40–50 psi room temperature nitrogen gas from an external source connected at port 112, through a bath pump 95, e.g. a small venturi pump or a vacuum pump. Bath pump 95 continuously draws a slight vacuum on bath 43 (−2 to −6 PSI or even more) through conduit 55 cooling the bath chamber to a few degrees below the saturation temperature of liquid nitrogen at atmospheric pressure. The vacuum in bath 43 is measured with a vacuum gauge located at port 150. Bath pump 95 ejects the boil-off gas of the bath chamber out vent 93 to atmosphere. Bath pump 95 is controlled by pump control 95' located in the control panel (not shown).

If there is a short interruption in a filling line and fill region 12 is accessed resulting in region 12 being non-sterile for a short period, the delivery path is shut down by closing on/off valve 40 and the rate of gas flow through purge housing 63 and diverter 76 is elevated to e.g., 50 CPH at 30 PSIG, by activating by-pass purge valve 138. By elevating the flow rate through purge housing 63 and diverter 76, microbial contaminants are prevented from entering nozzle 60 and system 10 need not be resterilized.

During normal operation the pressure at the nozzle is monitored by a pressure sensor 128 (FIG. 5) located on the exterior of upper housing 30 at a port 104 and connected to conduit 54 via by-pass conduit 74 at a point upstream of nozzle flow-control restriction 65.

Prior to cool-down mode, sterilization mode is entered in order to sterilize lower housing 50 and the delivery path downstream of filter 45. With on/off valve 40 and bath valve 92 closed, bath pump 95 off and a valve 114, located within float valve 47 for closing off flow through float valve 47, closed, sterilizing media, i.e., matter or radiation (including hot fluid, hot gas, electromagnetic radiation, ultraviolet light, y-radiation or chemical agents) is introduced into a third flow path to sterilize filter 45 and the delivery flow path downstream of filter 45. It is particularly useful to be able to do this quickly and efficiently.

Referring to FIGS. 4 and 5, liquid nitrogen within the delivery flow path is first drained through drain 101 by opening drain valve 132. The sterilizing media, e.g., hot (temperature depends on sterilization time, generally 400° F. or more) sterile inert fluid such as nitrogen gas, is then introduced into lower housing 50 from an external source (not shown). Hot gas is conducted through a gas valve 134 to a heater 100 connected to drain tap 101 via conduit 120. Hot gas entering drain tap 101 fills reservoir 44, travels through filter 45 to conduit 58, through coil 38 and metering valve 42, into conduit 54 and through by-pass conduit 74 to port 104, sterilizing these components. The hot gas also flows through flow restriction orifice 65 and out nozzle 60, sterilizing this path as well. By-pass conduit 74 increases the heating efficiency by allowing a high gas flow rate, i.e., by avoiding flow-control restriction 65 in nozzle 60.

Hot gas is vented out port 104 by opening vent valve 126. A temperature sensor 130 located at port 104 measures the temperature of the exiting gas to verify flow of the hot gas. Any nitrogen gas in bath 43 resulting from conductive heating through inner walls 34 and 82 is vented through bypass valve 94.

Purge housing 63 and diverter 76 are also both sterilized before system start-up. With purge valve 138 and diverter valve 140 closed, hot gas enters purge housing 63 and diverter 76 through gas valve 134 (FIG. 5).

By keeping the number of parts and their respective masses that need be sterilized to a minimum, the overall sterilization cycle time and ensuing cool down time are kept to a minimum.

After a predetermined time (established experimentally by the time required to kill microbial contaminants), the sterilization cycle is ended and the cool-down mode entered followed by the operational mode.

Lower housing 50 is easily accessible for service by removing a "V"-band coupling 25 and sliding off a cylindrical cap 51 surrounding filter 45. Purge housing 63 is removable for servicing the nozzle by means of a "V"-band clamp and sanitary flange and gasket 73.

Filter 45 is of stacked disc construction, with a 0.2 micron absolute rating for bacteria retention. It is held in place by "V"-band coupling 25 which includes a spring washer that compresses a teflon O-ring and makes a tight seal throughout the full range of temperature conditions. Liquid flows from the outside of the filter through the membrane discs, to the interior where it is then sterile. The differential pressure determined by comparing readings from pressure transducer 99 with readings from pressure sensor 138 indicates if filter 45 becomes clogged. If filter 45 is clogged, the differential pressure will increase indicating that service of filter 45 is required. Filter 45 is easily accessible for replacement by removing cylindrical cap 51.

In general, the device has smooth cleanable outside contours minimizing crevices where contaminants can collect. Additionally, there are no areas in the device where sterilizing media could collect. This is particularly important if a sterilizing media other than gas is utilized, which could cause blockage upon freezing when liquid nitrogen is entered into the system if the sterilizing media was not completely drained from the system.

Referring to FIG. 6, in an additional embodiment, liquid nitrogen is delivered to upper housing 30 from integrated local phase separator 160. The liquid nitrogen in separator 160 is at equilibrium with atmospheric vapor pressure, so its temperature is maintained at the boiling point of liquid nitrogen at atmospheric pressure. Liquid nitrogen enters separator 160 via conduit 162. Nitrogen gas from triax conduit 164 exits separator 160 through conduit 166. An jumper hose 168 connects a vacuum jacket of separator 160 to the vacuum jacket of bayonet connector 20. The vacuum is maintained by a vacuum pump (not shown) connected to vacuum port 170.

In an alternative embodiment, the filter, which has sufficient surface area to allow both liquid and gas to flow through with no adverse pressure drop, and the subcooling coils are capable of recondensing gas to liquid. It is therefore possible to eliminate float valve 47 and simply allow the liquid/gas mixture to flow on through the rest of the unit.

To shorten the sterilization cycle, an additional path may be added in order to heat liquid nitrogen within bath 43 by hot gas entering port 106 regulated by gas valve 134 and exiting through vent by-pass valve 94 regulated by valve control 94'.

In an alternative embodiment, the sterilization process may be sped up by draining liquid nitrogen within bath 43 through port 106 prior to the introduction of hot gas by pressurizing bath 43 and opening a second drain valve (not shown).

In an alternative embodiment, system 10 may be automatically controlled by a central controller connected to various valve controllers (not shown). To use the system, a user pushes a start button which activates the central controller to begin the sterilization cycle. The central controller then operates various valves as follows. Drain valve 132 is automatically opened to drain liquid nitrogen within lower housing 50 and conduit 54. Drain valve 132 is then closed and gas valve 134 opened to allow gas to enter heater 100 where it is heated to a desired temperature. From heater 100, hot gas flows into lower housing 50, purge housing 63 and diverter 76. Hot gas may also flow into bath 43 if desired.

After the predetermined time, the sterilization cycle is ended and the cool-down mode automatically entered. Gas valve 134 is closed and bath valve 92 and by-pass valve 94 are opened. Purge valve 138 and diverter valve 140 are also opened to allow room temperature nitrogen gas to flow therethrough.

Once the system has reached liquid nitrogen temperature, operational mode is automatically entered. On/off valve 40 is opened and a desired level of liquid nitrogen within bath 43 is maintained by cycling bath valve 92 controlled by sensor 102. Bath pump 95 is automatically activated. Nozzle pressure is automatically controlled by metering valve 42. The central controller is in communication with an assembly line, responding to activation and deactivation of the assembly line by turning on diverter 76 to interrupt flow out nozzle 60.

Other embodiments are within the following claims.

What is claimed is:

1. A system for delivering a controlled stream of sterile liquid cryogen from an outlet, comprising a cryogen delivery flow path including a delivery conduit connecting a source of liquid cryogen to the outlet, a cryogen sterilizer capable of sterilizing cryogen flowing therethrough, said cryogen sterilizer being positioned in the delivery conduit, the delivery conduit comprising a sterile delivery conduit section downstream of the cryogen sterilizer, an on/off valve positioned between the cryogen sterilizer and the liquid cryogen source, a sterilizing flow path for sterilizing the cryogen sterilizer and the sterile delivery conduit section, the sterilizing flow path comprising a sterilizing conduit communicating between a source of sterilizing medium and a connection to the cryogen delivery flow path, said on/off valve being positioned between said connection and said cryogen source, whereby the cryogen sterilizer and the sterile delivery conduit section can be isolated from the liquid cryogen source during sterilization such that sterilization occurs without subjecting the liquid cryogen source to the sterilizing medium.

2. The system of claim 1 wherein the cryogen sterilizer is a filter having pores sized to sterilize the fluid passing therethrough.

3. The system of claim 2 wherein the filter is constructed of hydrophobic polytetrafluoroethylene (PTFE).

4. The system of claim 3 wherein the filter is a 0.2 micron filter.

5. The system of claim 1 wherein the sterilizing medium comprises a sterile inert gas and the sterilization conduit is a conduit suitable for conveying the sterile inert gas.

6. The system of claim 5 wherein the system further comprises a heater for raising the temperature of the sterile inert gas.

7. The system of claim 6 further comprising a gas valve which regulates delivery of the sterile inert gas to the sterilization conduit.

8. The system of claim 1 wherein the sterile delivery conduit section comprises a flow-control restriction, and the system further comprises a sterilization medium by-pass conduit positioned to connect a sterilization medium outlet to a point in the sterile delivery conduit section upstream of the flow-control restriction, the sterilization medium by-pass conduit functioning to increase flow of the sterilizing medium through the cryogen sterilizer.

9. The system of claim 8 wherein the by-pass conduit comprises apparatus for verifying flow of said sterilizing medium through the system.

10. The system of claim 9 wherein the apparatus for verifying flow includes a temperature sensor to measure the temperature of the sterilizing media.

11. The system of claim 10 wherein the temperature sensor is positioned adjacent said sterilization medium outlet.

12. The system of claim 7 further comprising a drain valve for regulating drainage of liquid cryogen from the cryogen sterilizer before sterilization.

13. The system of claim 1 wherein the fluid flowing through the cryogen sterilizer sustains heat leak resulting in the fluid being saturated.

14. The system of claim 13 wherein gas in the saturated fluid is vented through a float valve.

15. The system of claim 1 further comprising a bath containing liquid cryogen which subcools sterile liquid cryogen in the sterile delivery conduit section, and means to supply liquid cryogen to, and to maintain liquid cryogen in, the bath.

16. The system of claim 15 further comprising a gas valve for regulating the entry of hot gas into the bath to heat the bath during sterilization.

17. The system of claim 6 or 16 further comprising a vent valve for regulating the venting of hot gas from the bath during sterilization.

18. The system of claim 17 further including a central controller for automatically controlling said system.

19. A method for delivering a controlled stream of sterile liquid cryogen from an outlet, the method comprising a) providing a system comprising:
   i) a cryogen delivery flow path conduit connecting a source of liquid cryogen to the outlet,
   ii) a cryogen sterilizer positioned in a section of the delivery flow path conduit, capable of sterilizing fluid flowing therethrough, the delivery flow path conduit comprising a sterile delivery conduit section downstream of the cryogen sterilizer; and
   iii) an on/off valve positioned between the cryogen sterilizer and the liquid cryogen source, b) delivering liquid cryogen from the source through the cryogen sterilizer and the sterile delivery conduit section downstream of the cryogen sterilizer to the outlet; and c) periodically sterilizing the cryogen sterilizer and the sterile delivery conduit section by delivering a sterilizing medium to a connection to the delivery flow path conduit positioned downstream of the on/off valve while the on/off valve is closed, whereby the cryogen sterilizer and the sterile delivery conduit section are isolated from the liquid cryogen source during sterilization, and sterilization occurs without subjecting the liquid cryogen source to the sterilizing medium.

20. The method of claim 19 wherein the sterilizing medium comprises a source of sterile nitrogen gas delivered into the cryogen sterilizer and the sterile delivery conduit section.

21. The method of claim 20 wherein liquid cryogen flow through the flow path conduit is stopped by closing said on/off valve, liquid cryogen in the delivery flow path is drained by opening a drain valve, and a gas valve is opened to introduce the sterile nitrogen gas.

22. The method of claim 19 wherein the cryogen sterilizer is a filter.

23. The method of claim 22 wherein the filter is a 0.2 micron filter constructed of hydrophobic polytetrafluoroethylene (PTFE).

24. The method of claim 19 wherein the fluid passing through the cryogen sterilizer further comprises saturated liquid cryogen.

* * * * *

UNITED STATES PATENT AND TRADEMARK OFFICE
CERTIFICATE OF CORRECTION

PATENT NO.    : 5,557,924
DATED         : SEPTEMBER 24, 1996
INVENTOR(S)   : RUSSELL BLANTON ET AL.

It is certified that error appears in the above-identified patent and that said Letters Patent is hereby corrected as shown below:

Column 7, line 5, replace "y-radiation" with --$\gamma$-radiation--.

Signed and Sealed this

Twelfth Day of September, 2000

Attest:

Q. TODD DICKINSON

*Attesting Officer*    *Director of Patents and Trademarks*